United States Patent
Purcell

(10) Patent No.: US 7,041,124 B2
(45) Date of Patent: May 9, 2006

(54) SYSTEM AND METHOD FOR PROVIDING THERAPY TO A PORTION OF A BODY

(75) Inventor: Ricky W. Purcell, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 167 days.

(21) Appl. No.: 10/745,392

(22) Filed: Dec. 23, 2003

(65) Prior Publication Data
US 2005/0137660 A1    Jun. 23, 2005

(51) Int. Cl.
*A61F 7/02*    (2006.01)

(52) U.S. Cl. ............ 607/112; 128/898; 607/96; 607/108

(58) Field of Classification Search ........ 128/898; 602/61; 607/112
See application file for complete search history.

(56) References Cited

U.S. PATENT DOCUMENTS

| | | | | |
|---|---|---|---|---|
| 2,807,262 A | * | 9/1957 | Lew | 602/47 |
| 4,366,804 A | | 1/1983 | Abe | |
| 4,516,564 A | | 5/1985 | Koiso et al. | |
| 4,832,030 A | * | 5/1989 | De Canto | 607/109 |
| 5,534,021 A | | 7/1996 | Dvoretzky et al. | |
| 5,658,583 A | | 8/1997 | Zhang et al. | 424/402 |
| 5,674,270 A | | 10/1997 | Viltro et al. | |
| 5,718,955 A | | 2/1998 | McGuire et al. | |
| 5,860,945 A | | 1/1999 | Cramer et al. | 602/62 |
| 5,904,710 A | * | 5/1999 | Davis et al. | 607/108 |
| 5,980,562 A | * | 11/1999 | Ouellette et al. | 607/108 |
| 6,102,937 A | | 8/2000 | Cramer et al. | |
| 6,656,210 B1 | * | 12/2003 | Plewes | 607/112 |
| 6,890,553 B1 | * | 5/2005 | Sun et al. | 424/449 |

FOREIGN PATENT DOCUMENTS

DE    20108752    11/2001

OTHER PUBLICATIONS

"International Search Report, for Application No. PCT/US2004/025861, date mailed Apr. 1, 2005", 14 pages.

* cited by examiner

*Primary Examiner*—Lee S Cohen
*Assistant Examiner*—Henry M Johnson, III
(74) *Attorney, Agent, or Firm*—Schwegman, Lundberg, Woessner & Kluth, P.A.

(57) ABSTRACT

The present invention relates to a system and method for providing therapy to a portion of a body. The system and method use an elastic band to hold a pack against an injured area on a body. The system and method are particularly effective in supporting packs that require access to the ambient environment in order to maintain a chemical reaction within the pack. The system comprises an elastic band that includes an opening and a pack that includes a gas-permeable portion. The pack is secured to the elastic band such that the gas-permeable portion of the pack is exposed through the opening in the elastic band. The elastic band provides support to the pack without covering the gas-permeable portions of the pack. Therefore, the elastic band does not inhibit the chemical reaction within the pack when the elastic band is applied to the portion of the body.

26 Claims, 6 Drawing Sheets

SYSTEM AND METHOD FOR PROVIDING THERAPY TO A PORTION OF A BODY

FIELD

This invention relates in general to a system and method for providing therapy to a portion of a body, and in particular to a system and method that use a elastic band to support the portion of the body.

BACKGROUND

Applying therapy to various parts of a body is a recognized practice for curing or alleviating multiple kinds of physical problems. One example therapy involves cooling an injured portion of a body by applying ice packs near the injured portion of the body in an effort to reduce swelling, inflammation and/or muscle pain. Another cooling method utilizes a cold pack that generates cooling via an endothermic chemical reaction which takes place within the cold pack.

Another example therapy utilizes heat to treat symptoms such as stiffness, muscle pain, cold hands and feet, lumbago, rheumatism and neuralgia (among others). Some known heat-treating methods include direct application of heat to the body using items such as a towel, jelly and/or paste. Another example heating therapy includes applying a heating pad to an injured portion of a body to alleviate discomfort caused by injury (e.g., muscular strain).

There are other heat-treating methods that utilize heat patches to apply heat to a body. One such heat patch generates heat via an exothermic chemical reaction that takes place within the heat patch. Heat patches that generate heat using an exothermic reaction typically include an enclosure and a heating composition stored within the enclosure. At least a portion of the enclosure is gas-permeable such that exposing the heating composition to air generates a heat-producing exothermic reaction within the heat patch.

Some other therapies include applying an analgesic (for pain) or an antibiotic (for infection) to the injured portion of the body. The analgesic and/or antibiotic may be incorporated into a pack/patch that is applied directly or indirectly to the body.

One concern with using heating pads and ice bags is that they are difficult to attach to an injured area of a body because they often need to be manually held in place by the injured person or someone assisting the injured person.

One method of maintaining hot or cold packs in place against an injured area of the body includes placing a pack against the body and wrapping a towel several times around the body such that the pack is sandwiched between the injured area and the towel. The free end of the towel is then is attached to an exposed and already-wrapped section of the towel to prevent the towel from unwinding.

Wrapping towels around the body in this manner can be quite cumbersome. Furthermore, the towels are seldom able to maintain a pack in its desired location, especially when a patient moves around. In addition, when a towel is wrapped more tightly around the body in an attempt to help keep the ice or cold pack in place, the towel may cause patient discomfort.

Another method of treating an injured area of a body includes using a elastic band to support the injured area of the body. Elastic bands may also be used to hold hot or cold packs against the injured area of the body.

As discussed above, many of the packs that generate a chemical reaction within the pack require access to the air in the ambient environment in order to maintain the chemical reaction. One concern with using a elastic band to secure this type of pack to a body is that the elastic band covers the gas-permeable portions of the pack thereby inhibiting the chemical reaction.

Another concern with using elastic bands to hold hot or cold packs against the injured area of the body is that they must typically be discarded along with the pack once the chemical reaction has expired within the pack. Therefore, an entirely new elastic band is required to hold a new pack against the injured area of the body.

Some elastic bands include pockets that are adapted to retain hot or cold packs. The packs are positioned against an injured portion of a body as the elastic band is wrapped around the body.

One drawback with including pockets in elastic bands is that the pockets add unwanted expense to the cost of producing elastic bands. A pocket also limits the size and/or number of pack(s) that may be inserted into the pocket. In addition, pockets often provide inadequate support to a pack, especially when the pocket is much bigger than the pack.

SUMMARY OF THE INVENTION

The present invention relates to a system and method for providing therapy to a portion of a body. The system and method use an elastic band to hold a pack against an injured area on a body. The system and method are particularly effective in supporting packs that require access to the ambient environment in order to maintain a chemical reaction within the pack.

In one aspect, the present invention relates to a system for providing therapy to a portion of a body. The system comprises an elastic band that includes an opening and a pack that includes a gas-permeable portion. The pack is secured to the elastic band such that the gas-permeable portion of the pack is exposed through the opening in the elastic band.

The elastic band provides support to the pack without covering the gas-permeable portions of the pack. Therefore, the elastic band does not inhibit a chemical reaction that may take place within the pack when the elastic band is applied to the portion of the body.

In some example forms of the system, a support at least partially surrounds the opening in the elastic band. The support may be a plastic film that has a lower elasticity than the elastic band.

In addition, the pack may be releasably secured to the support on the elastic band such that the system may further include another pack that can be secured to the elastic band after the original pack is released from the elastic band. The new pack may similarly include a gas-permeable portion that is exposed through the opening in the elastic band when the new pack is releasably secured to the elastic band.

One reason for replaceable packs is that some packs, such as packs that maintain a chemical reaction within the pack, have limited operating life. Therefore, releasably securing the packs to the elastic band facilitates replacement of expired packs without having to dispose of the elastic band.

In another aspect, the present invention relates to a system for providing therapy to a portion of a body. The system comprises an elastic band that includes an opening, and a pack that is secured to the elastic band. The pack includes an enclosure and a heating composition that is sealed within the enclosure. The enclosure includes a gas-permeable portion that is exposed through the opening in the elastic band.

The heating composition generates heat when a gas, such as air, is supplied from the ambient environment to the heating composition through the gas-permeable portion of the enclosure. The opening in the elastic band allows the elastic band to support the body without inhibiting the heating composition's access to the ambient air.

In yet another aspect, the present invention relates to a method of applying therapy to a portion of a body. The method includes securing a pack to an elastic band such that a gas-permeable portion of the pack is exposed through an opening in the elastic band. The method further includes wrapping the elastic band around the body such that the pack engages the injured portion of the body.

In some sample forms of the method, wrapping the elastic band around the body such that the pack engages the injured portion of the body includes using the pack to apply a topical medication and/or transdermal medication to the injured portion of the body.

Securing the pack to the elastic band may also include releasably securing the pack to the elastic band. When the pack is releasably secured to the elastic band, the method may further include unwrapping the elastic band from around the body; releasing the pack from the elastic band; securing another pack to the elastic band such that a gas-permeable portion of the second pack is exposed through the opening in the elastic band; and wrapping the elastic band around the body such that the new pack engages the injured portion of the body.

The purposes and features of the present invention will be set forth in the description that follows. Additional features of the invention will be realized and attained by the product and processes particularly pointed out in the written description and claims hereof, as well as from the appended drawings.

BRIEF DESCRIPTION OF THE DRAWINGS

The present invention will be more fully understood, and further features will become apparent, when reference is made to the following detailed description and the accompanying drawings. The drawings are merely representative and are not intended to limit the scope of the claims. Like parts depicted in the drawings are referred to by the same reference numerals.

DETAILED DESCRIPTION OF THE INVENTION

In the following detailed description, reference is made to the accompanying drawings, which show specific embodiments in which the invention may be practiced. These embodiments are described in sufficient detail to enable those skilled in the art to practice the invention. It is to be understood that other embodiments may be utilized and structural changes made, such that the following detailed description is not to be taken in a limiting sense.

Figure 1:
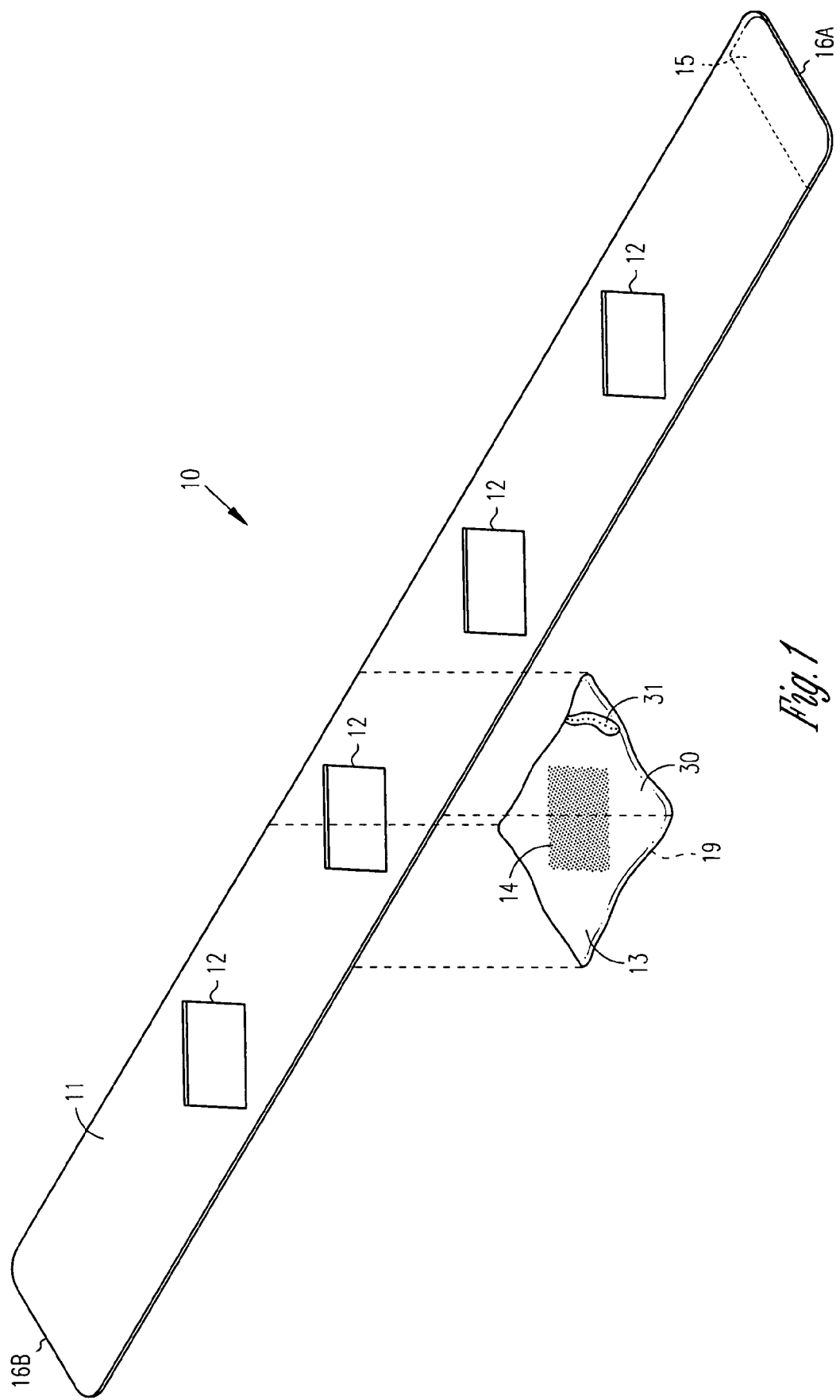
FIG. 1 is an exploded perspective view of a system.
Figure 2:
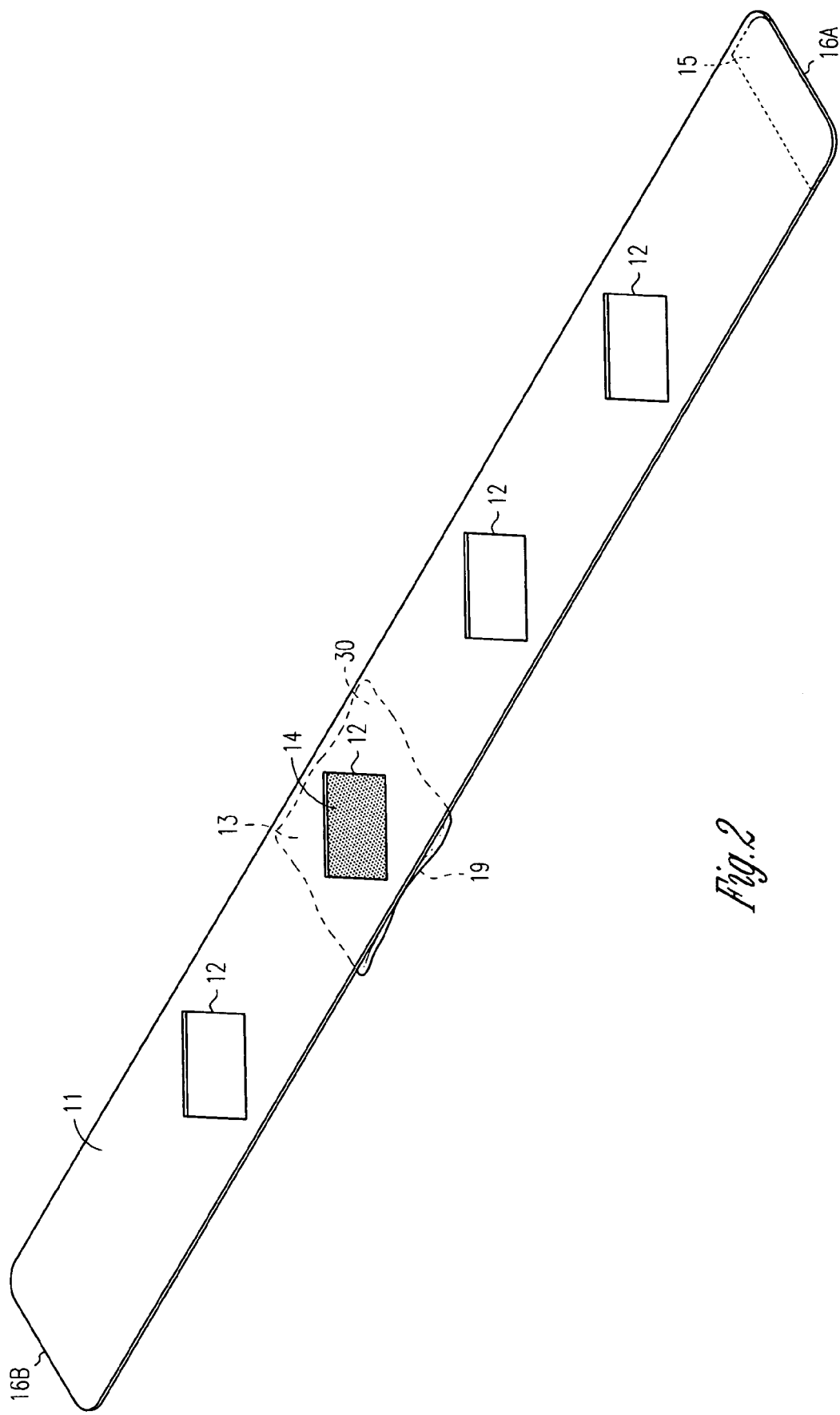
FIG. 2 is a perspective view of the system shown in FIG. 1.

FIG. 1 illustrates a system 10 for providing therapy to a portion of a body. The system 10 includes an elastic band 11 having one or more openings 12. The system 10 further includes a pack 13 having a gas-permeable portion 14. As shown in FIG. 2, the pack 13 is secured to the elastic band 11 such that the gas-permeable portion 14 of the pack 13 is exposed through the opening 12 in the elastic band 11.

The elastic band 11 may be formed from one or more of layers (only one layer is shown in FIGS. 1 and 2). The number and type of layers will depend on the application where the system 10 is used. As an example, some layers may be more elastic while other layers may be made of softer and/or more insulating materials. The elastic band 11 may be made out of an elastomeric non-woven material or a non-woven laminate. The elastic band 11 may be created by folding material in half and securing the edges of the material together using adhesives, or some other known fastening techniques.

The proper size and shape of the elastic band 11 will also depend on the application where the system 10 is used. The appropriate length and width will be determined in part by the size and shape of the injured portion on the body. In some forms, the elastic band 11 may be long enough to fit around the arms, legs, head or torso of a human being.

The system 10 may further include an adhesive, such as adhesive layer 15, which is mounted on the elastic band 111 near an end 16A of the elastic band 11. The adhesive layer 15 is adapted to initially secure the elastic band 11 relative to the body before the elastic band 11 is wrapped around the injured portion of the body.

In some forms, a cover (not shown) may be detachably mounted to the adhesive layer 15. The cover is removed to expose the adhesive layer 15 so that the adhesive layer 15 can be used to initially secure the elastic band 11. The adhesive may be styrene-isoprene-styrene copolymer, silicone or hydrogel, although any conventional adhesive may be used. In some example forms, the adhesive 15 may be a hook-and-loop fastener.

The system 10 is applied to the body by initially securing the pack 14 to the elastic band 11 such that the gas-permeable portion 14 of the pack 13 is exposed through the opening 12 in the elastic band 11. The elastic band 11 is then secured relative to the body at a location near the injured portion of the body.

Once the elastic band 11 is secured relative to the body, the elastic band 11 is wrapped around the injured portion of the body 100. The elastic band 11 is wrapped around the body until a second end 16B of the elastic band 11 is secured to an already-wrapped and exposed section of the elastic band 11. The second end 16B may be tucked into an already-wrapped section of the elastic band 11, or secured using any type of fastener (e.g., a hook-and-loop fastener).

In some forms, the pack 13 may include an adhesive (not shown) on the side of the pack 13 that is opposite to the elastic band 11. The pack 13 may then be initially placed against the body with pressure before being further secured by the elastic band 11.

Figure 3:
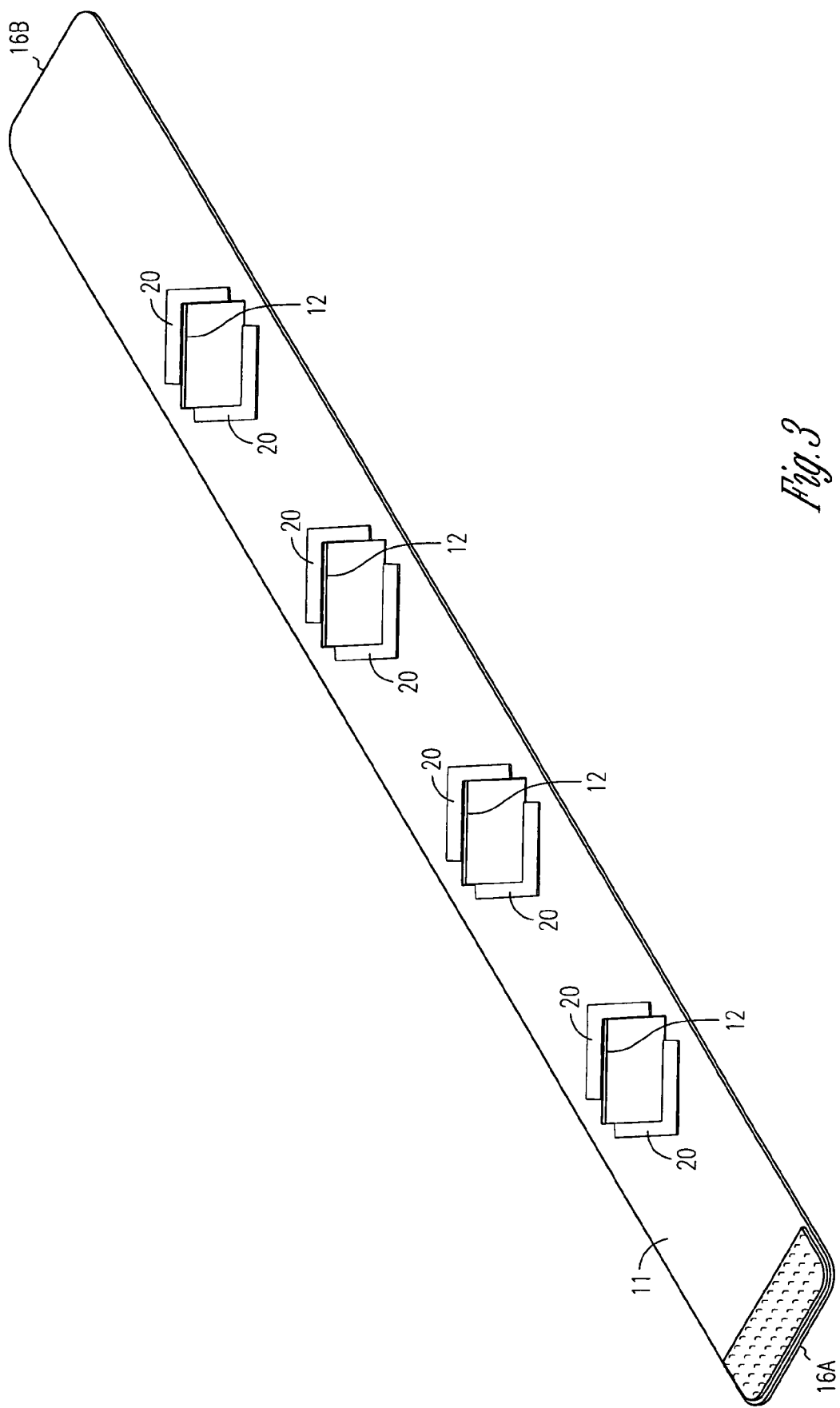
FIG. 3 is a perspective view of another elastic band that may be used in the system of FIG. 1.
Figure 4:
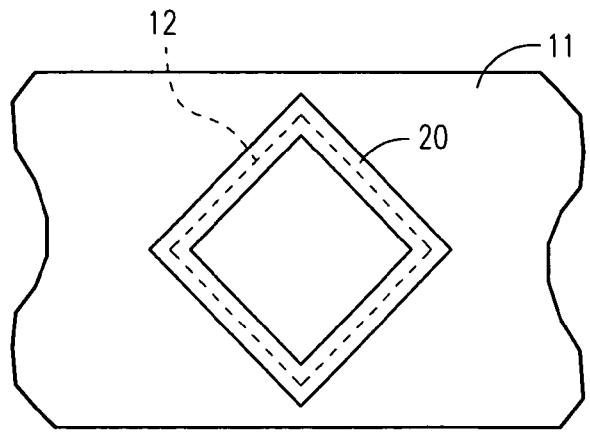
FIG. 4 is a plan view illustrating a portion of another elastic band that may be used in the system of FIG. 1.

As shown in FIG. 3, the system 10 may further include a support 20 that at least partially surrounds the opening 12 in the elastic band 11. In some forms, the support 20 surrounds the entire opening 12 (see, e.g., FIG. 4). The support 20 may have a lower elasticity than the elastic band 11 to provide stability to the elastic band 11 near the opening 12. As an example, the support 20 may be a plastic film, although other materials may be used.

In some forms, the pack 13 may include an adhesive that is releasably secured to the support 20. It should be noted that the adhesive may be a chemical adhesive or a hook-and-loop type fastener.

Figure 5:
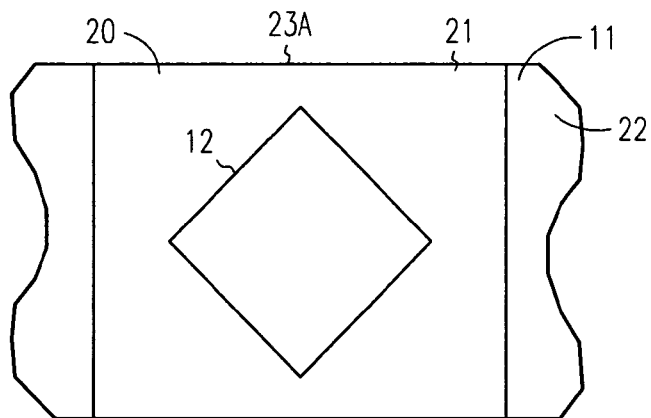
FIG. 5 is a plan view illustrating a portion of still another elastic band that may be used in the system of FIG. 1.

In the example embodiment illustrated in FIG. 5, the support 20 is formed of a layer 21 that partially covers one side 22 of the elastic band 11. In some forms, the support extends between lateral sides 23A, 23B of the elastic band 11.

Positioning the support 20 around the opening 12 minimizes the stress that is generated on the opening 12 when the elastic band 11 is stretched as part of being wrapped around the body. The location and orientation of the support 20 relative to the elastic band 11 and the pack 13 allows the pack 13 to be more reliably secured to the elastic band 11.

As shown in FIG. 1, the pack 13 may include an enclosure 30 and a heating composition 31 that is sealed within the enclosure 30. The heating composition may be capable of generating heat when a gas (e.g., ambient air) is supplied to the heating composition 31 through the gas-permeable portion 14 of the enclosure 30. As an example, the heating composition 31 may be any combination of an iron powder, water, a water-retaining agent, a reaction promoter and a salt.

In some embodiments, the gas-permeable portion 14 of the enclosure 30 may be aligned with the opening 12 in the elastic band 11. In addition, the gas-permeable portion 14 of the enclosure 30 may be substantially the same size as the opening 12 in the elastic band 11.

Figure 6:
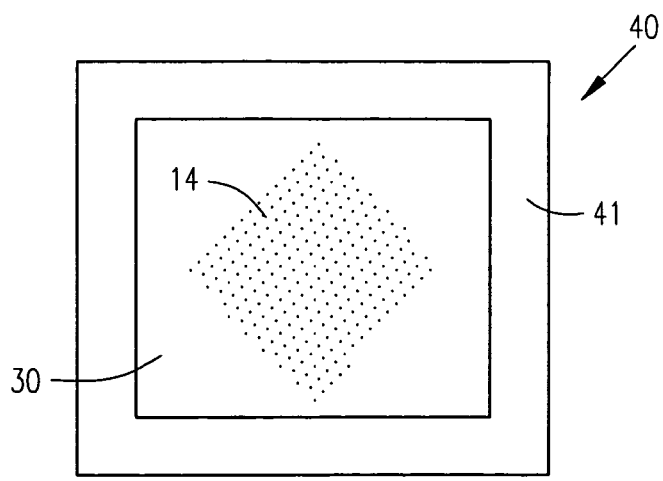
FIG. 6 is a plan view illustrating another pack that may be used in the system of FIG. 1.

FIG. 6 shows an example embodiment of another type of pack 40 that may be secured to the elastic band 11. The pack 40 is similar to the pack 13 in that pack 40 includes an enclosure 30 having a gas-permeable portion 14. The pack 40 further includes a portion 41 that provides support to the elastic band 11 around the opening 12 in the elastic band 111 when the pack 40 is secured to the elastic band 11 (pack 40 not shown secured to elastic band 11 in FIG. 6).

It should be noted that in any of the embodiments shown and described herein, one or more packs 13, 40 may include a medication, such as a transdermal and/or topical medication, that is applied to the portion of the body (see, e.g., medication 19, which is on the underside of pack 13 in FIGS. 1 and 2). In some forms, the transdermal and/or topical medication may be part of an adhesive that is used to apply the packs 13, 40 to the body.

In addition, the elastic band 11 and or the packs 13, 40 may be treated with a variety of therapeutic additives, such as herbs, vitamins and/or botanicals. Some example botanicals include lavender, chamomile, moisturizers, lipids, essential oils and fragrances. The therapeutic additives could be sprayed, or gravure printed, directly on the elastic band 11 and/or the packs 13, 40.

It should be noted the packs, 13, 40 may also include non-steroidal anti-inflammatory drugs. Some example non-steroidal anti-inflammatory drugs include aspirin, ibuprophen, ketoprophen and naproxen sodium (among others). In some forms, the non-steroidal anti-inflammatory drugs will be available by prescription only.

In some forms, packs 13, 40 may be applied to an affected skin area to deliver treatment from various skin ailments. Some example ailments include irritation due to sun burns, heat burns, insect bites, athletes foot, dry skin, or other chronic skin conditions.

Figure 7:
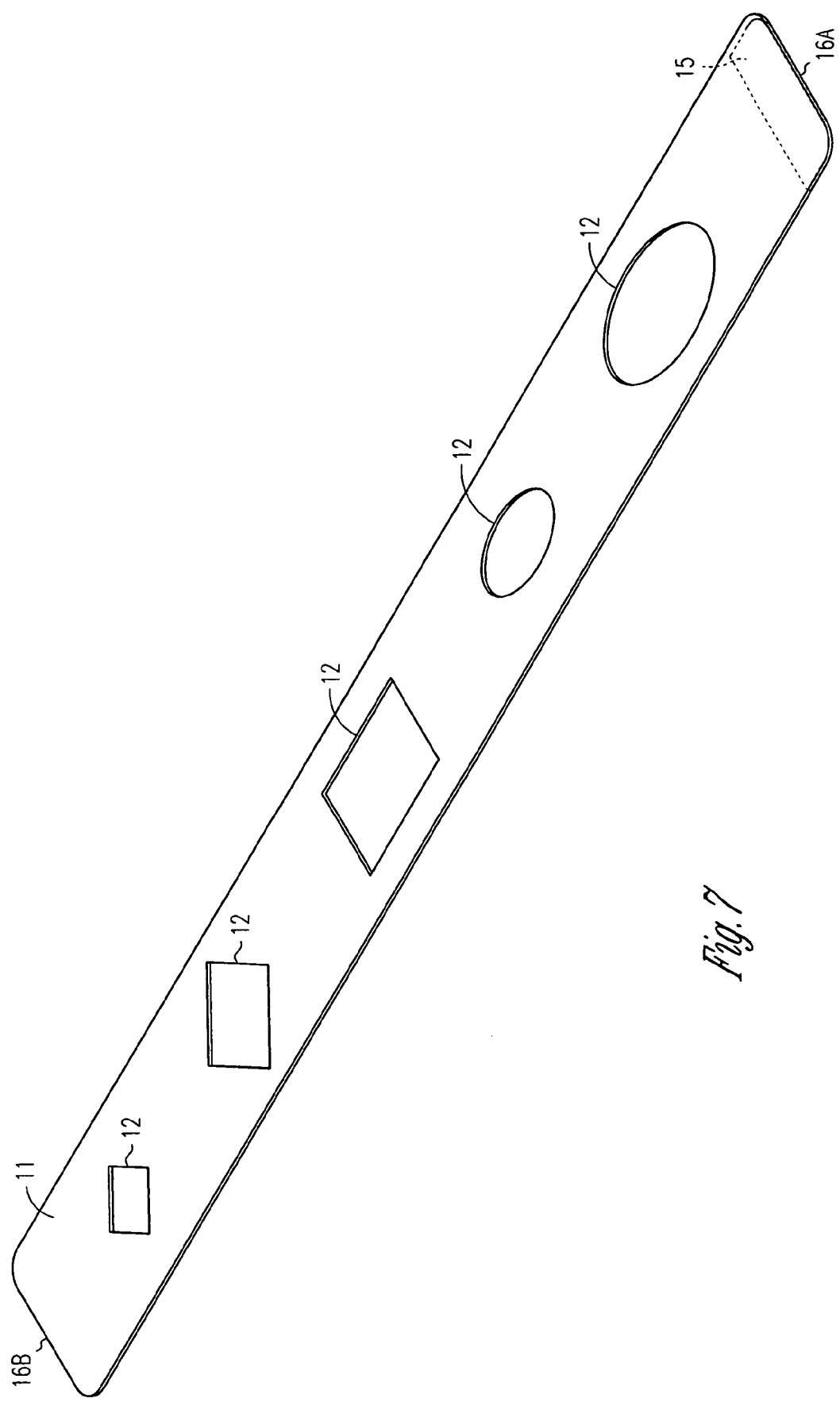
FIG. 7 is a plan view illustrating yet another elastic band that may be used in the system of FIG. 1.

Although the openings 12 in FIGS. 1–3 are shown as diamond-shaped, FIG. 7 shows that size and shape of the openings 12 may vary. It should be noted that the number, size, shape and arrangement of the openings 12 and packs 13, 40 may vary, and will depend in large part on the application where the system 10 is being used.

In some example embodiments, the pack is a first pack (e.g., pack 13) that may be releasably secured to the elastic band 11. In some forms, the system 10 further includes a second pack (e.g., pack 40) that is the same or different than the first pack. The second pack can be releasably secured to the elastic band 11 after the first pack is released from the elastic band 11. The second pack may similarly include a gas-permeable portion 14 that is exposed through the opening 12 in the elastic band 11 when the second pack is releasably secured to the elastic band 11.

Releasably securing packs to the elastic band 11 allows replacement packs to be positioned against the injured area of the body without having to use a replacement elastic band. Replacing packs is especially important in applications where the packs include compositions which generate heat via a chemical heat reaction. Once the chemical reaction expires, or slows too far down, a replacement pack is easily attached to the same elastic band 11.

Figure 8:
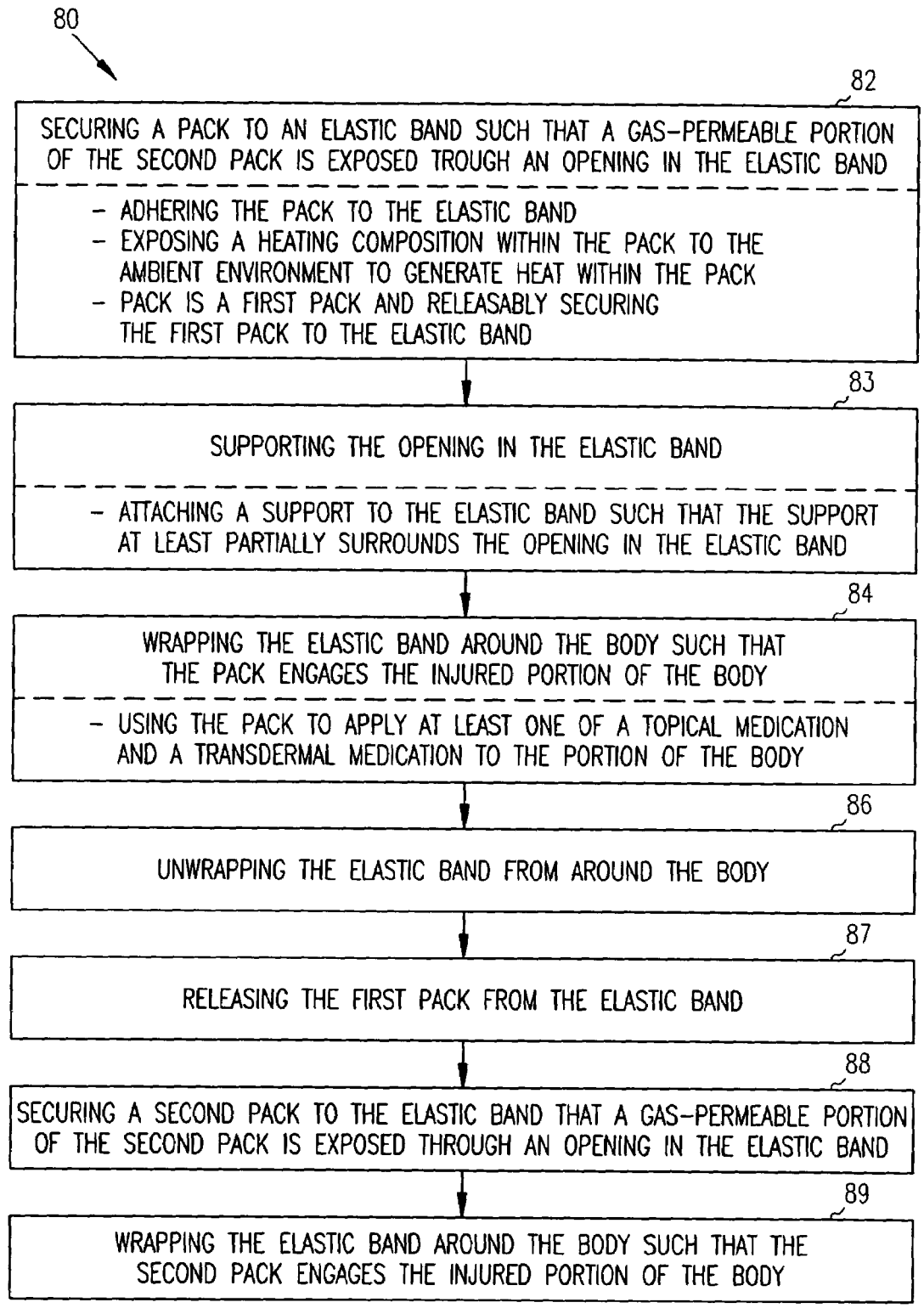
FIG. 8 is a flow diagram illustrating a method of applying therapy to a portion of a body.

A method 80 of applying therapy to a portion of a body is described herein with reference to FIG. 8. The method 80 includes securing a pack to an elastic band such that a gas-permeable portion of the pack is exposed through an opening in the elastic band [82]. The method further includes wrapping the elastic band around the body such that the pack engages the injured portion of the body [84]. The method may further include supporting the opening in the elastic band [83].

Securing a pack to an elastic band such that a gas-permeable portion of the pack is exposed through an opening in the elastic band [82] may include (i) exposing a heating composition within the pack to the ambient environment to generate heat within the pack; and/or (ii) adhering the pack to the elastic band. In some forms, supporting the opening in the elastic band [83] may include attaching a support to the elastic band such that the support at least partially surrounds the opening in the elastic band. In addition, wrapping the elastic band around the body such that the pack engages the injured portion of the body [84] may include using the pack to apply at least one of a topical medication and a transdermal medication to the portion of the body.

It should be noted that the pack may be a first pack such that securing the first pack to the elastic band [82] may include releasably securing the first pack to the elastic band. When the first pack is releasably secured to the elastic band, the method may further include unwrapping the elastic band from around the body [86]; releasing the first pack from the elastic band [87]; securing a second pack to the elastic band such that a gas-permeable portion of the second pack is exposed through an opening in the elastic band [88]; and wrapping the elastic band around the body such that the second pack engages the injured portion of the body [89].

The operations discussed above with respect to the described methods may be performed in a different order from those described herein. In addition, FIGS. 1–8 are representational and are not necessarily drawn to scale. Certain proportions thereof may be exaggerated, while others may be minimized.

While the invention has been described in detail with respect to the specific aspects thereof, it will be appreciated that those skilled in the art, upon attaining an understanding of the foregoing, may readily conceive of alterations to, variations of, and equivalents to these aspects which fall within the spirit and scope of the present invention, which should be assessed accordingly to that of the appended claims.

I claim:

1. A system for providing therapy to a portion of a body, the system comprising:
   an elastic band that includes an opening that extends through the elastic band; a support element attached to said elastic band, the support element at least partially surrounds said opening that extends through said elastic band without covering said opening that extends through said elastic band; and
   a pack that includes a gas-permeable portion, said pack being secured to said elastic band such that said gas-permeable portion of said pack is exposed through said opening in said elastic band.

2. The system of claim 1 wherein said support surrounds said entire opening that extends through said elastic band without covering said opening that extends through said elastic band.

3. The system of claim 1 wherein said support has a lower elasticity than said elastic band.

4. The system of claim 1 wherein said pack includes an adhesive that is releasably secured to said support.

5. The system of claim 1 wherein said support is formed of a layer that partially covers one side of said elastic band.

6. The system of claim 5 wherein said elastic band includes lateral sides and said support extends from one lateral side to the other lateral side.

7. The system of claim 1 wherein said support is a plastic film.

8. The system of claim 1 wherein said pack includes an enclosure and a heating composition sealed within said enclosure, the heating composition being capable of generating heat when a gas is supplied to said heating composition through said gas-permeable portion of said enclosure.

9. The system of claim 8 wherein said gas-permeable portion of said enclosure is aligned with said opening in said elastic band.

10. The system of claim 9 wherein said gas-permeable portion of said enclosure is substantially the same size as said opening in said elastic band.

11. The system of claim 8 wherein said heating composition is any combination of an iron powder, water, a water-retaining agent, a reaction promoter and a salt.

12. The system of claim 8 wherein said pack includes a transdermal medication that is applied to the portion of the body.

13. The system of claim 8 wherein said pack includes a topical medication that is applied to the portion of the body.

14. The system of claim 1 wherein said pack is secured to said elastic band such that a portion of said pack provides support to said elastic band around said opening in said elastic band.

15. The system of claim 1 wherein said opening in said elastic band is diamond-shaped.

16. The system of claim 1 wherein said pack is releasably secured to said elastic band.

17. The system of claim 16 wherein said pack is a first pack, the system further comprising a second pack that can be secured to said elastic band after the first pack is released from the elastic band, the second pack including a gas-permeable portion that is exposed through said opening in said elastic band when said second pack is releasably secured to said elastic band.

18. A system for providing therapy to a portion of a body, the system comprising:
   an elastic band that includes an opening which extends through the elastic band; a support element attached to said elastic band, the support element at least partially surrounds said opening that extends through said elastic band without covering said opening that extends through said elastic band; and
   a pack releasably secured to said elastic band, wherein said pack includes an enclosure and a heating composition sealed within said enclosure, wherein said enclosure includes a gas-permeable portion that is exposed through said opening in said elastic band, said heating composition being capable of generating heat when a gas is supplied to said heating composition through said gas-permeable portion of said enclosure.

19. The system of claim 18 wherein said pack includes at least one of a topical medication and a transdermal medication that are applied to the portion of the body.

20. The system of claim 18 wherein said gas-permeable portion of said enclosure is aligned with said opening in said elastic band and is substantially the same size as said opening in said elastic band.

21. A method of applying therapy to a portion of a body, the method comprising:
   securing a pack to an elastic band such that a gas-permeable portion of the pack is exposed through an opening which extends through the elastic band;
   wrapping the elastic band around the body such that the pack engages the injured portion of the body; and
   supporting the opening in the elastic band, wherein supporting the opening in the elastic band includes attaching a support to the elastic band such that the support at least partially surrounds the opening in the elastic band.

22. The method of claim 21 wherein securing a pack to an elastic band includes adhering the pack to the elastic band.

23. The method of claim 21 wherein securing a pack to an elastic band such that a gas-permeable portion of the pack is exposed through an opening in the elastic band includes exposing a heating composition within the pack to the ambient environment to generate heat within the pack.

24. The method of claim 21 wherein wrapping the elastic band around the body such that the pack engages the injured portion of the body includes using the pack to apply at least one of a topical medication and a transdermal medication to the portion of the body.

25. The method of claim 21 wherein the pack is a first pack, and securing the first pack to the elastic band includes releasably securing the first pack to the elastic band.

26. The method of claim 25 further comprising:
   unwrapping the elastic band from around the body;
   releasing the first pack from the elastic band;
   securing a second pack to the elastic band such that a gas-permeable portion of the second pack is exposed through an opening in the elastic band; and
   wrapping the elastic band around the body such that the second pack engages the injured portion of the body.

* * * * *